United States Patent [19]

Murata

[11] 4,450,429
[45] May 22, 1984

[54] HUMIDITY SENSITIVE RESISTANCE DEVICE
[75] Inventor: Michihiro Murata, Kyoto, Japan
[73] Assignee: Murata Manufacturing Co., Ltd., Japan
[21] Appl. No.: 436,663
[22] Filed: Oct. 26, 1982
[51] Int. Cl.³ .............................................. H01L 7/00
[52] U.S. Cl. ..................................... 338/35; 338/308; 73/336.5; 252/520
[58] Field of Search .......................... 338/35, 308–309; 252/518, 520; 73/335, 336.5, 73, 335

[56] References Cited
U.S. PATENT DOCUMENTS 3,671,913 6/1983 Mariya et al. ........................ 338/35
4,263,576 4/1981 Murata et al. ........................ 338/35
4,374,760 2/1983 Charles ................................. 252/518

Primary Examiner—C. C. Shaw
Assistant Examiner—Christopher N. Sears
Attorney, Agent, or Firm—Ostrolenk, Faber, Gerb & Soffen

[57] ABSTRACT

A humidity sensitive resistance device, including opposing electrodes (102, 103) formed on an insulating substrate (101), and a humidity sensitive resistance film (104) formed on the surface of the insulating substrate (101) and at least between the opposing electrodes (102, 103). The resistivity of the humidity sensitive resistance film (104) increases with an increase of an ambient relative humidity. The humidity sensitive resistance film (104) comprises a hydrophilic polymer and a conductive powder, and has a zirconium compound unevenly distributed on the side of surface thereof. The surface of the humidity sensitive resistance film (104) is dehydrated by contact with an alkaline solution or by heating.

16 Claims, 12 Drawing Figures

HUMIDITY SENSITIVE RESISTANCE DEVICE

BACKGROUND OF THE INVENTION

1. Field of the Invention

The present invention relates to a humidity sensitive resistance device for detecting the change of an ambient humidity as a function of the change of resistance value.

2. Description of the Prior Art

It has been known that a dispersed mixture including conductive powder and resin exhibits a change in its resistance value according to the change of an ambient humidity. An attempt has been made to use the dispersed mixture for a humidity sensitive device by utilizing such property. However, since repeated hysteresis of detecting a humidity involves the migration of the conductive powder in the resin, a disadvantage is encountered in terms of responsibility, reproducibility or hysteresis.

In order to remove such disadvantage, another attempt has been made to prevent the conductive powder from migrating in the resin by bridging the resin with an organic compound cross-linking agent. According to this attempt, the migration of the conductive powder may be repressed with the strength of the resin film increasing. Nevertheless, another disadvantage is encountered in that wetability becomes so poor that detecting ability may be decreased.

SUMMARY OF THE INVENTION

The present invention aims to provide a humidity sensitive resistance device having high sensitivity for humidity and high responsiveness and exhibiting excellent hysteresis characteristics and the like.

The present invention comprises a humidity sensitive resistance device including a humidity sensitive resistance film, the humidity sensitive resistance film comprising a hydrophilic polymer and a conductive powder, and having a zirconium compound unevenly distributed on the side of surface of the resistance film, and the surface of the resistance film being dehydrated.

More specifically, the humidity sensitive resistance device is so constructed that the humidity sensitive resistance film is formed on electrodes opposed to each other and the resistivity of the humidity sensitive resistance film increases with an increase of an ambient relative humidity, and is characterized in that the humidity sensitive resistance film comprises the hydrophilic polymer and the conductive powder, and has a zirconium compound unevenly distributed on the side of surface of the resistance film, and the surface of the resistance film is dehydrated.

When the humidity sensitive resistance film of such structure takes up water vapor, the electrical contact of the conductive particles with each other is cut off by the swelling of the resin and as a result the electrical resistance of the film is increased.

These objects and other objects, features, aspects and advantages of the present invention will be more apparent from the following detailed description when taken in conjunction with the accompanying drawings.

DESCRIPTION OF THE PREFERRED EMBODIMENTS

Figure 1:
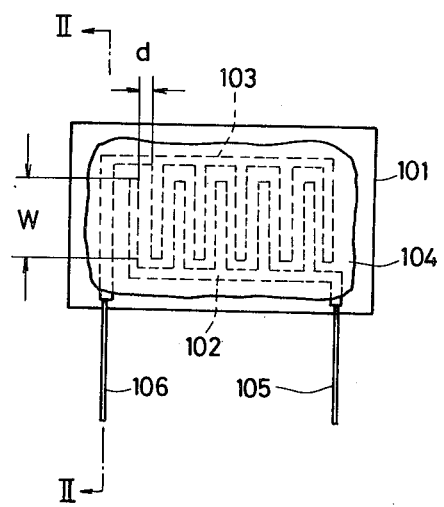
FIG. 1 is a plan view showing one embodiment of the inventive humidity sensitive resistance device.
Figure 2:
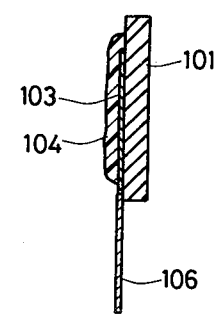
FIG. 2 is a sectional view taken along the line II—II in FIG. 1.

FIGS. 1 and 2 show one embodiment of the inventive humidity sensitive resistance device. The humidity sensitive resistance device shown comprises an insulating substrate 101 of such as glass, ceramics and the like and opposing electrodes 102 and 103 formed on the insulating substrate 101. The opposing electrodes 102 and 103 are configured in a comb-shape, such that tooth portions thereof are mutually interdigitated or interleaved. A humidity sensitive resistance film 104 is formed on the insulating substrate 101 so as to cover the surface of the insulating substrate 101 where the opposing electrodes 102 and 103 are formed. As a result, the humidity sensitive resistance film 104 is formed on the surface of the insulating substrate 101 and at least between opposing electrodes 102 and 103. Lead terminals 105 and 106 are electrically connected to the end portions of the respective opposing electrodes 102 and 103 for the purpose of external connection.

A characteristic of the present invention is that a zirconium compound exists in a state unevenly distributed on the surface side of a humidity sensitive resistance film including a hydrophilic polymer and a conductive powder, and the surface of the humidity sensitive resistance film is dehydrated.

For achieving the unevenly distributed of the zirconium compound on the side of surface of the humidity sensitive resistance film, the following process may be adopted.

A paste is prepared to contain the hydrophilic polymer and the conductive powder, and then a film of this paste is formed on a suitable insulating substrate. Then, the zirconium compound is applied to the film by immersing this film in a solution containing the zirconium compound, or by spraying or painting the film with a solution containing the zirconium compound, whereby the zirconium compound is unevenly distributed on the side of surface of the film. The main point is that the zirconium compound is mainly distributed on the side of surface of the film before treatment in an alkaline solution described below. Then, the film, on the side of surface of which the zirconium compound has been maldistributed, is dehydrated at its surface.

The dehydration is carried out as follows.

The film is brought into contact with an alkaline solution or is immersed in an alkaline solution, and the film is then washed and dried. Alternatively, the film may be subjected to vapor of an alkaline solution, and dried. In this case, washing may be omitted. This procedure results in the dehydration reaction of a hydrophilic group (OH group) of glycol bonding in the hydrophilic polymer with the zirconium compound, whereby the surface of the humidity sensitive resistance film comes to be firm and to have high durability against water. As a result, a humidity sensitive resistance device having stable characteristics and high reliability can be obtained.

More specifically, since, according to the above described dehydration, the solubility of the surface of the humidity sensitive resistance film in water is lowered, that is, the durability of it against water is enhanced, it turns out that the film cannot be dissolved in the presence of water, and the structure of the film becomes stable against water.

On the other hand, the inner region of the humidity sensitive resistance film mainly consists of the hydrophilic polymer and the conductive powder. In this region, the electrical contact of the conductive particles with each other is cut off by the swelling of the polymer and as a result the electrical resistance of the resistance film is increased.

The dehydration may be also caused by heating, instead of the above described treatment in the alkaline solution. The heating temperature may be so selected that a dehydration reaction may be caused by heating. For example, the reaction is rapidly concluded at a temperature of 100° C. or above.

The conductive powder as a part of the inventive humidity sensitive resistance film may be carbon powder, for example; however, alternatively other conductive material of compounds, metals or the like may be used for the conductive powder. The conductive powder of not more than 10μ grain size is preferable for obtaining a good property for response performance.

Furthermore, for example, a polyvinyl alcohol group polymer, a mixture of polyvinyl alcohol and a cellulose derivative, partially hydrolyzed product of polymethyl acrylate, partially hydrolyzed product of polyethyl acrylate or the like may be used as the hydrophilic polymer.

The above described polyvinyl alcohol group polymer includes:

(1) Completely or partially hydrolyzed products of polymers or copolymers of vinyl acetate and/or other various vinyl esters;

(2) Hydrolyzed products of copolymers obtained by copolymerization of vinyl acetate and/or other various vinyl esters with various unsaturated monomers, such as α-olefines, vinyl chloride, acrylonitrile, acrylamide, acrylic esters, or methacrylate esters; and (3) Polyvinyl alcohol group polymers obtained by esterification of the above described polyvinyl alcohol group polymers with cyclic acid anhydrides, or polyvinyl alcohol group polymers modified with carboxyl groups.

The above described cellulose derivative includes diacethylcellulose, methylcellulose, ethylcellulose, hydroxycellulose, carboxydimethylcellulose, and cyanoethylcellulose.

Furthermore, for the zirconium compound having compatibility with the hydrophilic polymer includes zirconium oxychloride, zirconium chloride, zirconium acetate, zirconium sulfate, for example, and other salts of zirconium. Zirconium compounds soluble in water or in alcohol are used.

The mixing ratio of each component of the hydrophilic polymer, and the zirconium compound having compatibility with the hydrophilic polymer and the conductive powder, which form the humidity sensitive resistance film having its resistability increasing with an increase of an ambient relative humidity, may be selected as follows.

The humidity sensitive resistance film comprises 20–80% by weight of the hydrophilic polymer, not more than 20% by weight of the zirconium compound, and 20–80% by weight of the conductive powder. The reason why 20–80% by weight of the hydrophilic polymer and 20–80% by weight of the conductive powder are included is that, if the percentage of the hydrophilic polymer is decreased below 20% by weight or the percentage of the conductive powder is increased beyond 80% by weight, then the variation of resistance value with absorption of moisture becomes small, while, if the percentage of the hydrophilic polymer goes up to over 80% by weight, or the percentage of the conductive powder is decreased below 20% by weight, then the inherent resistance value of the humidity sensitive resistance film becomes large to such an extent that it is impossible to use it for a practical use. Further, the reason why not more than 20% by weight of the zirconium compound is included is that, if the percentage of it goes up to over 20% by weight, then the extent of swelling of the humidity sensitive resistance film by absorption of water becomes small and the variation of the resistance value becomes small. In the following, the present invention will be further described in accordance with specific examples in detail.

EXAMPLE 1

Polyvinyl alcohol was dissolved in a mixture of alcohol and ethyleneglycol monobutyl ether. Carbon black powder of 30 mμ average grain size was added to the above described solution with an equal amount to 100 parts by weight of the polyvinyl alcohol, whereupon the solution was mixed up to provide paste. On the other hand, as shown in FIG. 1, an insulating substrate 101 was prepared with comb-shaped carbon electrodes 102 and 103 being formed thereon, the electrode distance d being 0.3 mm and the total of each electrode opposing distance W being 6.5 cm. The above described paste was painted on the insulating substrate 101 to cover the carbon electrodes 102 and 103.

Next, the insulating substrate thus obtained was immersed in an aqueous solution of 0.5% alcohol containing 0.2% zirconium oxychloride hydrate, pulled up from the solution, and thereafter dried, whereby the zirconium compound was applied to the painted film. Furthermore, the insulating substrate was immersed in an alkaline solution to establish the dehydration reaction between polyvinyl alcohol and zirconium compound. Thereafter, the insulating substrate was washed and dried. Then, the insulating substrate was heated. Different samples were obtained by differentiating such heating condition, that is, the samples were heated at temperatures of 100° C., 150° C. and 180° C., respectively.

Figure 3:
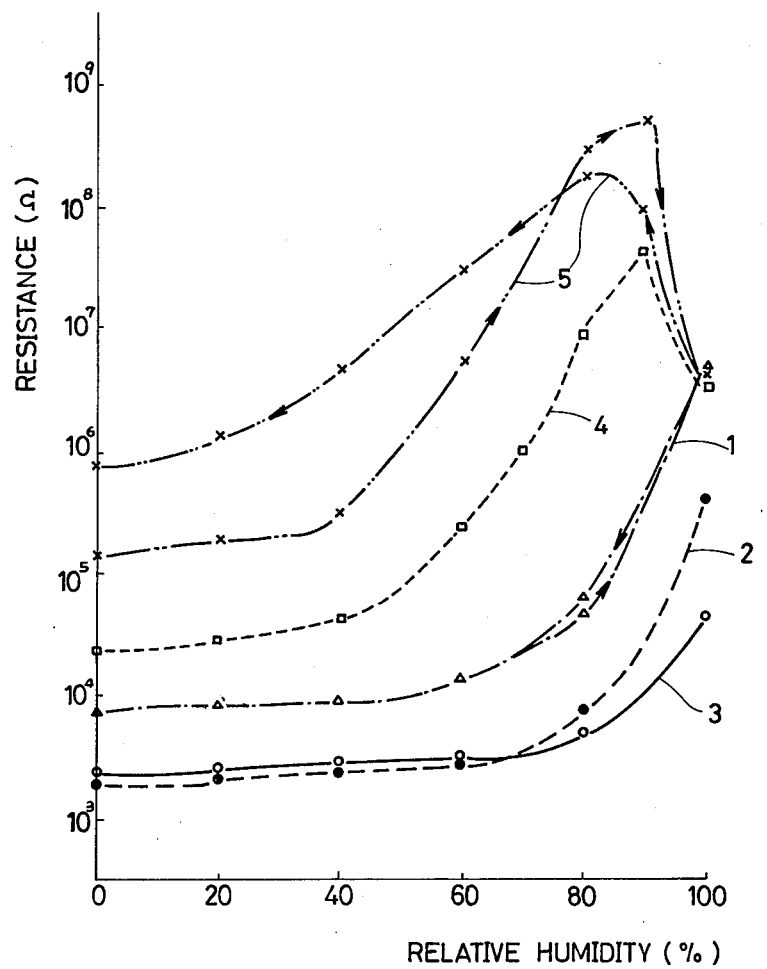
FIG. 3 is a graph showing resistance-relative humidity characteristics of humidity sensitive resistance devices obtained by Example 1.

The change of the resistance value of each humidity sensitive resistance device thus obtained was measured under several humidity conditions. The result of the measurement is shown in FIG. 3. In FIG. 3, the numeral 1 denotes the sample heated at 100° C., the numeral 2 denotes the sample heated at 150° C., and the numeral 3 denotes the sample heated at 180° C. In addition, the numerals 4 and 5 denote samples free from zirconium compound and being beyond the scope of the present invention, wherein the sample denoted by the numeral 4 was heated at 100° C. and the sample denoted by the numeral 5 was heated at 180° C.

As seen from FIG. 3 the samples according to the present invention exhibit the characteristic of a large resistance value variation in the region of higher humidity, and have small hysteresis effect. On the other hand, the samples not containing zirconium compound as shown by the numerals 4 and 5 have the maximum value at a relative humidity of about 90% in the curves showing resistance-relative humidity characteristics, have large hysteresis effect, and further suffer from the defect that the initial resistance value (the resistance value at relative humidity of 0%) is too high.

EXAMPLE 2

A film formed of paste containing zirconium compound was formed on an insulating substrate similar to that of Example 1. The sample was not immersed in an alkaline solution but heated at a temperature of 150° C. to allow the polyvinyl alcohol to react with the zirconium compound, whereby a humidity sensitive resistance device was obtained.

Figure 4:
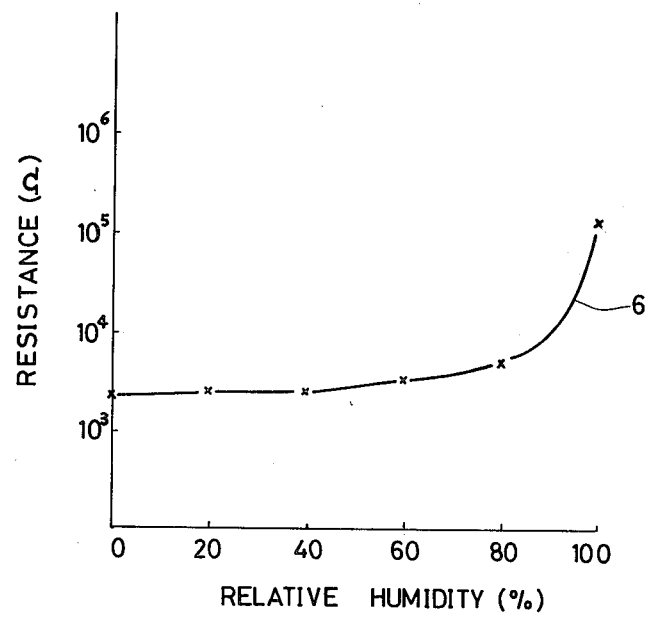
FIG. 4 is a graph showing a resistance-relative humidity characteristic of a humidity sensitive resistance device obtained by Example 2.

A resistance-relative humidity characteristic of the humidity sensitive resistance device thus obtained was measured. The result of the measurement is denoted by the numeral 6 in FIG. 4. As seen from FIG. 4, the humidity sensitive resistance device has a large resistance value variation in the region of higher humidity.

EXAMPLE 3

A sample was prepared in a similar manner as Example 1 with treatment in an alkaline solution and succeeding heat treatment at a temperature of 150° C. The respective resistance values of this sample were measured in dried and dew conditions. The result of the measurement was that the resistance value in the dried condition was 2 kΩ and the resistance value in the dew condition was 7.1 MΩ. The same sample was then subjected to repetition of alternating dried and dew conditions. After the procedure was repeated 500 times, the resistance value in a dried condition was 2.2 kΩ and the resistance value in a dew condition was 8 MΩ. The above described result means that there is little problem in the practice use and that a humidity sensitive resistance device having stable characteristics can be obtained.

EXAMPLE 4

Figure 5:
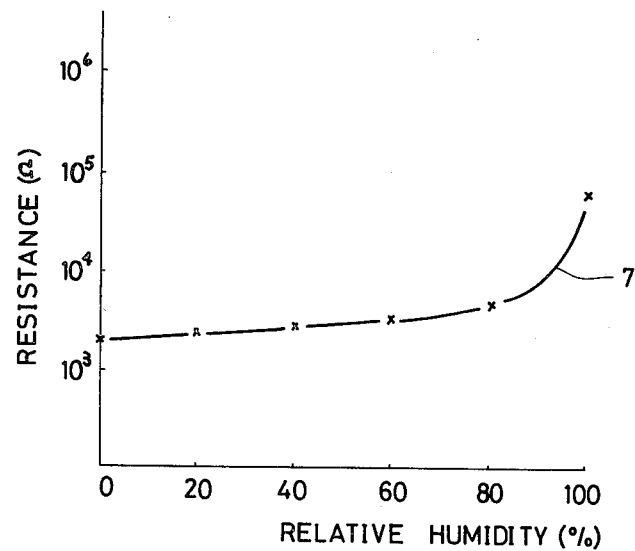
FIG. 5 is a graph showing a resistance-relative humidity characteristic of a humidity sensitive resistance device obtained by Example 4.

The sample described here are substantially the same as one described in Example 1, except for treatment with zirconium compound. The treatment was carried out with aqueous solution of 0.5% alcohol containing 2% of a zirconium oxychloride hydrate. In addition, the temperature of heating after washing was 150° C. A resistance value-relative humidity characteristic of this humidity sensitive resistance device was measured. The result of the measurement is denoted by the numeral 7 in FIG. 5. As shown in FIG. 5, the resulting humidity sensitive resistance device has a large resistance value variation in the region of higher humidity.

EXAMPLE 5

Polyvinyl alcohol was dissolved in the mixture of alcohol and ethyleneglycol monobutyl ether. On the other hand, ethylcellulose was dissolved in ethyleneglycol monobutyl ether. These mixed solutions were so mixed that 70 parts by weight of polyvinyl alcohol combine with 30 parts by weight of ethylcellulose, and further 100 parts by weight of carbon black powder of 30 m$\mu$ average grain size were added, and triturated to obtain paste. The paste was painted on an insulating substrate similar to that in Example 1.

Next, the insulating substrate was immersed in an aqueous solution of 0.5% alcohol containing 0.2% of a zirconium oxychloride hydrate to apply a zirconium compound to the painted film, pulled out and then dried. Furthermore, the insulating substrate was immersed in an alkaline solution to cause a reaction, thereafter washed and dried. Then, the same was heated at a temperature of 100° C., whereby a sample was obtained. The resistance value variation of the humidity sensitive resistance device thus obtained was measured in several humidity conditions. The result of the measurement is denoted by the numeral 8 in FIG. 6.

Figure 6:
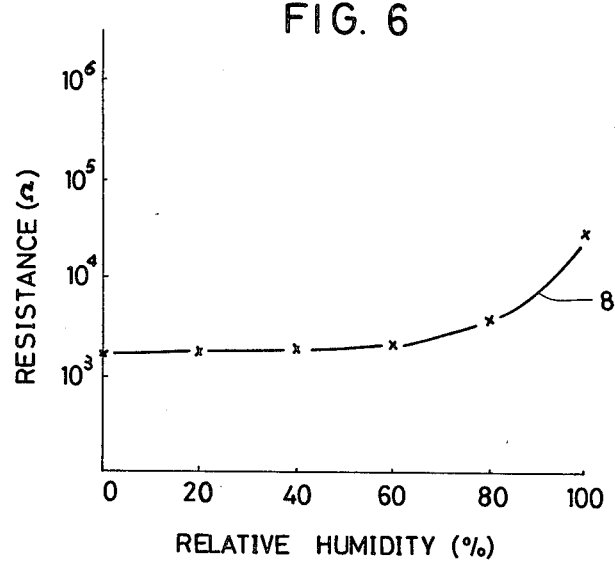
FIG. 6 is a graph showing a resistance-relative humidity characteristic of a humidity sensitive resistance device obtained by Example 5.

As seen from FIG. 6, the humidity sensitive resistance device of Example 5 has a large resistance value variation in the region of higher humidity.

EXAMPLE 6

Similarly to Example 1, paste was painted on insulating substrates. After being dried, the insulating substrates were immersed in the zirconium acetate solutions, respectively. Each concentration of zirconium acetate in these solutions was 0.5% and 5%, respectively. The respective samples were dried and then heated at a temperature of 150° C. The resistance value variation of each of the samples was measured in several humidity conditions. Both of the samples exhibited large resistance value variations in the range of higher relative humidity, wherein the resistance values were 2–3 kΩ at a relative humidity of 40%, 5–8 kΩ at 80%, and 150–300 kΩ at 100%.

Since the inventive humidity sensitive resistance device comprises a humidity sensitive resistance film comprising a hydrophilic polymer and a zirconium compound having compatibility with the hydrophilic polymer which both lead to a reaction product upon contact with an alkaline solution or by heating, the strength of the humidity sensitive resistance film can be increased without a lowering of wetability, the humidity sensitive characteristic is satisfactory, and the hysteresis of the humidity sensitive characteristic is small. Furthermore, since the reaction product of the hydrophilic polymer and the zirconium compound introduces zirconium in combination with oxygen which makes the thermal conductivity of the polymer higher and makes the humidity sensitive characteristic rise, the inventive humidity sensitive resistance device exhibits an excellent response for humidity. Furthermore, if the treatment in an alkaline solution is applied, the treatment can be carried out at room temperature, as a result, the humidity sensitive resistance device having an excellent characteristic can be obtained through a simple procedure.

As described above, the present invention relates to a humidity sensitive resistance device having a resistance characteristic wherein the resistivity thereof increases with an increase of an ambient relative humidity. According to a humidity sensitive resistance device having such characteristic, a dew sensor as given below will be advantageously obtained.

Figure 7:
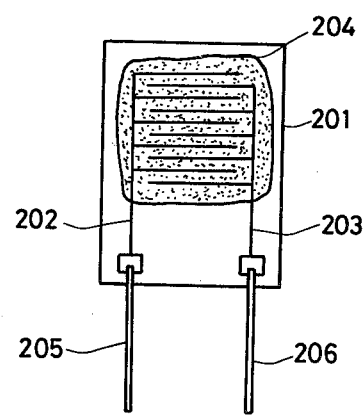
FIG. 7 is a plan view showing a dew sensor as another embodiment of the present invention.

FIG. 7 shows a dew sensor as another embodiment of the present invention.

In this figure, the numeral 201 denotes a substrate, on which comb-shaped detecting electrodes 202 and 203 are formed. On the substrate 201, a dew detecting film 204 having a relative humidity-resistance characteristic with a positive gradient is formed to cover the detecting electrodes 202 and 203. A feature of this dew sensor is that the substrate 201 is made of resistance material. As for the resistance material for the substrate 201, $SnO_2$ system material $TiO_{2-x}$ system material ($0 < X < 2$) or the like may be used. The resistance value of the substrate 201 is higher than that of the dew detecting film 204 in an ordinary humidity state, and close to the resistance value of the dew detecting film 204 in a dew state. In either state, the resistance value of the dew sensor is measured with the detecting electrodes 202 and 203. The numerals 205 and 206 denote lead wires.

According to such arrangement, the resistance of the dew detecting film is connected in parallel with the resistance due to the substrate 201. In an ordinary humidity state, the resistance due to the dew detecting film 204 substantially contributes to the resistance measured by the detecting electrodes 202 and 203, since the resistance of the dew detecting film 204 is lower than that of the substrate 201. On the other hand, in a dew state, the resistance of the dew defecting film 204 becomes higher. In this state, the resistance due to the dew detecting film 204 is detected through the detecting electrodes 202 and 203 in a similar manner as the above described lower resistance state of the dew detecting film 204. However, when the resistance value of the dew detecting film 204 shows some scatter in a dew state so that the resistance value becomes higher than the prescribed level, the resistance value of the substrate 201 becomes relatively lower than that of the dew detecting film 204 so that the resistance value of the dew sensor is governed by the resistance level determined by the resistance of the substrate 201 with the result that the resistance value due to the substrate 201 is substantially detected. Accordingly, it is necessary for the resistance value of the substrate 201 only to be previously set to the resistance value of the prescribed detecting level.

Figure 8:
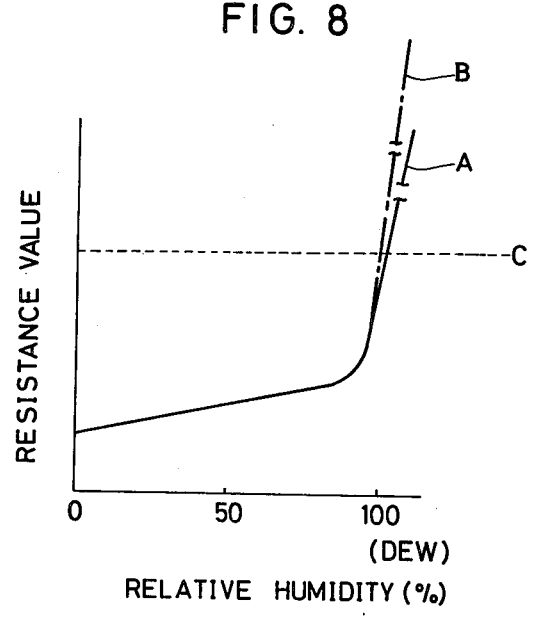
FIG. 8 is a graph showing typical resistance-relative humidity characteristics of dew sensors in accordance with the present invention for explanation of advantages of the embodiment shown in FIG. 7.

FIG. 8 is a graph showing typical resistance-relative humidity characteristics of dew sensors in accordance with the present invention. In this figure, the solid line A represents an idealized characteristic for relative humidity-resistance relationship of a dew sensor, and the dotted line B represents a relative humidity-resistance characteristic of a dew sensor causing some scatter. The broken line C represents the resistance level of the substrate 201, for example, in case of FIG. 7.

Accordingly, as apparent from the foregoing description, even if there is a possibility that the relative humidity-resistance characteristic of a dew sensor varies from sensor to sensor based on the varied resistance value due to the dew detecting film thereof, the scatter of the characteristic of the dew sensor can be minimized because the resistance level in a dew state is usually determined by the resistance of the substrate 201. Furthermore, the output level thereof can be kept constant and, therefore, the design for a detecting circuit may be facilitated. Furthermore, when the resistance value of the dew detecting film 204 becomes higher than that of the substrate 201 in a dew state, substantially all the electric current flows through the substrate 201, so that the electric current through the dew detecting film 204 becomes negligibly small. Therefore, the embodiment has the effect of prolonging the life of the dew sensor and minimizing the worsening of the characteristic of the dew sensor.

Figure 9:
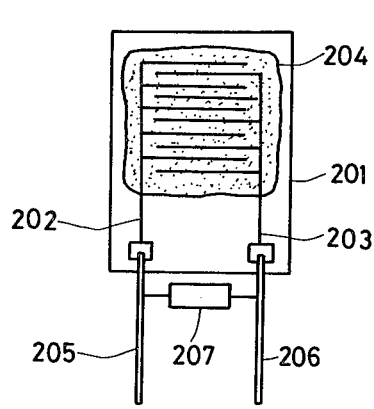
FIG. 9 is a plan view showing a dew sensor as a third embodiment of the present invention.

FIG. 9 shows another example of a dew sensor according to the present invention.

A feature of the dew sensor shown in FIG. 9 is that a substrate 201 is made of insulating material, but lead wires 205 and 206, connected with detecting electrodes 202 and 203, respectively, are connected through a fixed resistance 207 with each other.

The resistance 207 has a larger value than the resistance of a dew detecting film 204 in an ordinary humidity state in a similar manner as the substrate 201 of a resistance material shown in FIG. 7. The resistance 207 is eletrically connected in parallel with the dew detecting film 204.

Figure 10:
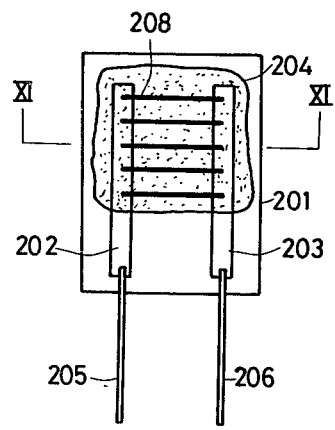
FIG. 10 is a plan view showing a dew sensor as a fourth embodiment of the present invention.
Figure 11:
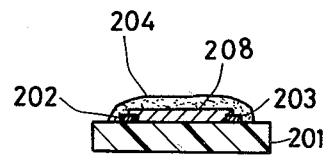
FIG. 11 is a sectional view taken along the line XI—XI in FIG. 10.

FIGS. 10 and 11 show further example of a dew sensor according to the present invention, wherein FIG. 10 is a plan view and FIG. 11 is a sectional view taken along the line XI—XI in FIG. 10.

A feature of the dew sensor shown in FIGS. 10 and 11 is that resistance films 208 are formed across opposed electrodes 202 and 203 on an insulating substrate 201, and a dew detecting film 204 is formed to cover the opposed electrodes 202 and 203 and the resistance films 208.

According to this example, the resistance due to the dew detecting film 204 is electrically connected in parallel with the resistance films 208.

Figure 12:
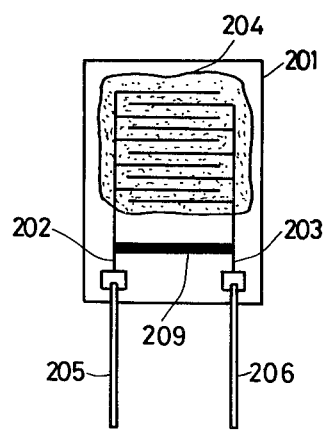
FIG. 12 is a plan view showing a dew sensor as the other embodiment of the present invention.

FIG. 12 shows a further example of a dew sensor according to the present invention.

A feature of the dew sensor shown in FIG. 12 is that comb-shaped detecting electrodes 202 and 203 are formed on an insulating substrate 201 and a dew detecting film 204 is formed on the insulating substrate 201 so as to cover the detecting electrodes 202 and 203, while a resistance film 209 connecting between the detecting electrodes 202 and 203 is formed on the remaining surface of the insulating substrate 201 left over after forming the dew detecting film 204.

According to this example, similarly to the embodiment shown in FIGS. 10 and 11, the resistance due to the dew detecting film 204 is electrically connected in parallel with the resistance film 209.

The above described examples shown in FIGS. 9 to 12 can obtain the same result as the example shown in FIG. 7.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A humidity sensitive resistance device wherein a humidity sensitive resistance film is formed on electrodes opposed to each other, and the resistivity of the humidity sensitive resistance film increases with an increase of an ambient relative humidity, characterized in that said humidity sensitive resistance film comprises a hydrophilic polymer and a conductive powder, and has a zirconium compound unevenly distributed on the side of surface of said film, and the surface of said film being dehydrated.

2. A humidity sensitive resistance device in accordance with claim 1, wherein, of the components of said humidity sensitive resistance film, said hydrophilic polymer and said conductive powder are in the proportions of 20-80% by weight of the former to 80-20% by weight of the latter.

3. A humidity sensitive resistance device in accordance with claim 1, said dehydration having been achieved by contact with an alkaline solution.

4. A humidity sensitive resistance device in accordance with claim 1, wherein said dehydration is achieved by heating.

5. A humidity sensitive resistance device in accordance with claim 1, wherein said hydrophilic polymer comprises at least one member selected from the group consisting of polyvinyl alcohol group polymer, a mixture of polyvinyl alcohol and a cellulose derivative, a partially hydrolyzed product of polymethyl acrylate, and a partially hydrolyzed product of polyethyl acrylate.

6. A humidity sensitive resistance device in accordance with claim 1, in which the particle size of said conductive powder is not more than 10 microns.

7. A humidity sensitive resistance device in accordance with claim 6, wherein the zirconium compound is not more than 20% by weight of said film.

8. A humidity sensitive resistance device in accordance with claim 7, wherein said hydrophilic polymer is polyvinyl alcohol.

9. A humidity sensitive resistance device in accordance with claim 8, wherein, of the components of said humidity sensitive resistance film, said hydrophilic polymer and said conductive powder are in the proportions of 20-80% by weight of the former to 80-20% by weight of the latter.

10. A humidity sensitive resistance device in accordance with claim 9, wherein said conductive powder is carbon powder.

11. A humidity sensitive resistance device in accordance with claim 10, wherein said zirconium compound is zirconium oxychloride.

12. A humidity sensitive resistance device in accordance with claim 1, wherein the zirconium compound is not more than 20% by weight of said film.

13. A humidity sensitive resistance device in accordance with claim 12, wherein said hydrophilic polymer is polyvinyl alcohol.

14. A humidity sensitive resistance device in accordance with claim 13, wherein, of the components of said humidity sensitive resistance film, said hydrophilic polymer and said conductive powder are in the proportions of 20-80% by weight of the former to 80-20% by weight of the latter.

15. A humidity sensitive resistance device in accordance with claim 14, wherein said conductive powder is carbon powder.

16. A humidity sensitive resistance device in accordance with claim 15, wherein said zirconium compound is zirconium oxychloride.

* * * * *